Figure 1:
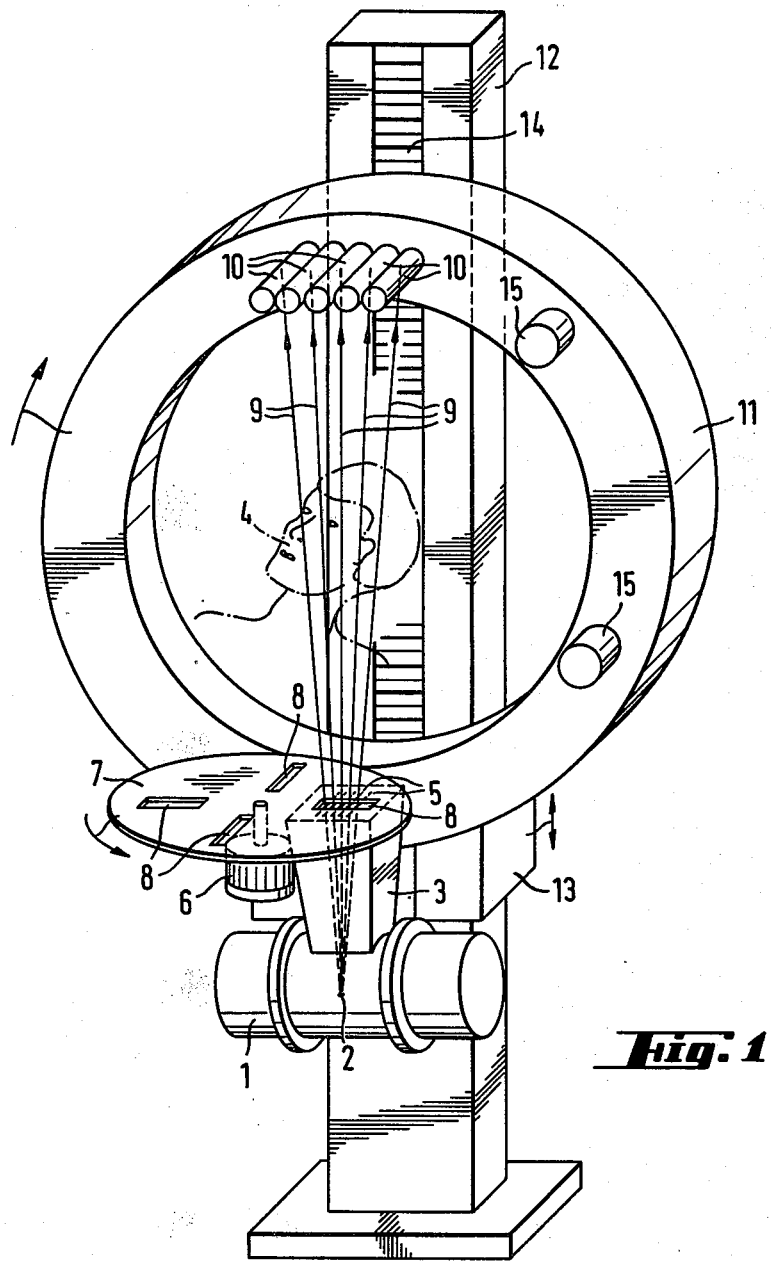

United States Patent [19]

Kinanen

[11] Patent Number: 4,481,650
[45] Date of Patent: Nov. 6, 1984

[54] INSTALLATION FOR PRODUCING RADIOGRAPHIC LAYER IMAGES

[75] Inventor: Ilmari Kinanen, Espoo, Finland

[73] Assignee: Instrumentarium Oy, Finland

[21] Appl. No.: 370,615

[22] Filed: Apr. 22, 1982

[30] Foreign Application Priority Data

Apr. 24, 1981 [FI] Finland ................................. 811281

[51] Int. Cl.³ ............................................. G03B 41/16
[52] U.S. Cl. .......................................... 378/7; 378/19
[58] Field of Search ............................... 378/19, 7, 22

[56] References Cited

U.S. PATENT DOCUMENTS

| | | | |
|---|---|---|---|
| 3,780,291 | 12/1973 | Stein | 378/146 |
| 4,135,095 | 1/1979 | Watanabe | 378/10 |
| 4,149,082 | 4/1979 | Haendle | 378/22 |
| 4,160,167 | 7/1979 | Weiss | 378/19 |
| 4,179,100 | 12/1979 | Sashen | 378/22 |
| 4,241,404 | 12/1980 | Lux | 378/19 |
| 4,277,684 | 7/1981 | Carson | 378/7 |

*Primary Examiner*—Craig E. Church
*Attorney, Agent, or Firm*—Andrus, Sceales, Starke & Sawall

[57] ABSTRACT

The purpose of the invention is to create a mechanically uncomplicated installation for producing radiographic layer images, making it possible to use small radiation dosages and, however, to collect sufficiently information on the object by one exposure, whereby separation of the superimposed layers from each other in a desired way for visualization can be accomplished by means of tomosynthesis. The installation includes radiation generating means (1, 2), collimating means for confining the radiation and focusing it on an object (4) to be radiographed, e.g. a patient, means (10) for detecting the radiation passed through the object and means for storing and processing the information contained in said detection. Said collimating means comprise a collimation unit (3) including at least two separate, narrow, contiguous, substantially parallel collimating slots (5) for producing narrow, fan-shaped beams, said slots being arranged preferably in alignment with the longitudinal axis of the object to be radiographed. The installation also includes means (11, 13) for displacing said collimating slots and the object to be radiographed in relation to each other at least substantially in alignment with the normal of said collimating slots, those parts of the object selected to be radiographed being arranged to be exposed to radiation by said narrow fan-shaped beams from a number of different directions. The information obtained from the object to be radiographed is stored preferably in digital form and processed for visualization.

18 Claims, 2 Drawing Figures

INSTALLATION FOR PRODUCING RADIOGRAPHIC LAYER IMAGES

The invention relates to an installation for producing radiographic layer images, said installation including penetrating radiation generating means, collimating means for confining the radiation and focusing it on an object, e.g. a patient, means for detecting the radiation passed through the object and means for storing and processing the information contained in said detections in a manner appropriate for visualization.

A special field of X-ray imaging is layer imaging or tomography. A layer image, tomogram, presents a sharp image of only a thin layer of the object to be radiographed. By arranging a collimated radiation beam to rotate round the object, simultaneously exposing the object to radiation from different directions and storing the radiation passed through the object on a film, a thin panoramic layer image of the object is produced. Thus a sharp image is obtained only of those parts of the object, the speed of the projections of which at the position of the film, due to the rotating movement of the beam, corresponds to the transmission speed of the film. Other parts of the object remain blurred. Consequently, a sharp image is produced of only one, thin panoramic layer, said layer being determined by film speed. However, except for certain special objects, e.g. dentition perhaps, it is generally difficult to know in advance which layer will give the most information on the object. Therefore, it is necessary to produce radiographs of a number of different layers, and consequently the patient is exposed to extra radiation.

In order to obtain enough information on the object for images representing different lateral layers, it has been suggested to take a number of separate, successive radiographs of the object from different directions by rotating a wide fan of beams covering the whole area to be radiographed round the object to be radiographed. These images are stored either optically by utilizing holography technique or electronically by means of e.g. videotechnique. Thus it is possible to select the particular layer that is desired to be sharp by utilizing the so called tomosynthesis technique based on the mutual, lateral movement of successively exposed different projection images placed or supposed to be placed on superimposed relationship with each other, and combining the images by summing them optically or electronically in a manner determined by the exposure delay factor representative of the selected layer depth. In spite of the fact that the information needed for planar tomographic images is obtained from the object by one exposure, the total dosage of radiation the patient is exposed to is fairly high. The resolution of the images depends on the dimensions of the separate detecting elements in the detector matrix.

For eliminating the relative movement between the radiation source and the object to be radiographed, solutions have been developed including a number of X-ray tubes, located in a circular fashion or in linear alignment, to be fired in rapid succession, and the images are stored for tomosynthesis. The addition to a fairly high radiation dosage, these solutions have the disadvantage of a complex and costly structure.

In order to reduce radiation dosage and improve resolution, a so called flying spot technique has been developed, according to which the object is scanned with an X-ray beam of a substantially restricted cross-section in both dimensions for producing conventional X-ray radiographs or images. In this case resolution is only dependent on the dimensions of the X-ray beams. The device can be constructed using mechanically fairly uncomplicated arrangements. When utilizing this technique electronic storage of information can be used with advantage by collecting only the information on the amount of radiation, arriving in the detector element and passed through the object, as a dependent variable of the location of the X-ray beams and by converting it into digital form, which enables an image to be directly produced by utilizing e.g. videotechnique. Disadvantages of this technique are the slowness of the scanning phase and the fact that the obtained information and images represent only conventional X-ray imaging, whereby all the superimposed layers in the object are imaged with equal sharpness without any possibility of separating different layers.

CT-scanners represent the most advanced technique enabling transaxial i.e. cross-section images to be produced of the object. According to this technique a beam of X-rays is rotated round the object to be radiographed so as to obtain information on the object from different view angles, the detection i.e. the radiation passed through the object are registered by e.g. a scintillation detector and the obtained information is converted into digital form, whereafter a cross-section image is reconstructed on the basis of the different projections with the aid of automatic data processing. One application is a scanner using a wide fan-shaped beam, covering in this dimension the whole object and having typically a thickness of appr. 1 cm, registering of the detections being accomplished by means of a detector unit wider or equal to the width of the fan-shaped beam and including a plurality of contiguous detector elements. The fan-shaped beam is moved round the object in width direction of the fan at the plane determined by the fan, whereby the layer reconstructed to an image is at the plane determined by the fan as well, and the thickness of the layer equals that of the fan. Due to the size of the fan-shaped beam and the great number of the detector elements, as well as to the complicated reconstruction of the image, the applications of this technique are costly. Resolution is dependent on the physical size of the detector elements. In order to reduce inaccuracies caused by diffuse radiation, the detector elements should be placed as close to the object to be radiographed as possible resulting in limited possibilities of imaging. Furthermore, the X-ray dosages the patients are exposed to are fairly high, and at one exposure enough information is received for only one cross-section image layer.

An object of the invention is to create a novel, mechanically uncomplicated and thus economical installation suited for layer imaging or tomography, enabling small radiation dosages and, nevertheless, collecting enough information on the object by one exposure for the visualization of selected superimposed layers with the aid of continuous tomosynthesis. Another object of the invention is to improve the resolution of the images produced. Still another aim is to eliminate the condition, setting limitations to imaging possibilities related to many X-ray imaging methods, that the detectors be placed as close to the object and the axis of the X-ray beam rotating movement as possible for improving the resolution. A further object is to increase information collecting speed. Finally, one further object of the invention is to produce an installation provided with the preceding characteristics for the electronic realization of panoramic radiography.

The objects of the invention are achieved in a way apparent from and described more closely in claim 1 and the subclaims. By using a sufficiently narrow fan-shaped beam, a better resolution is achieved in that particular dimension, while smaller radiation dosages are ensured. When using a number of separate parallel beams, the imaging process can be speeded up. In addition, information on the object to be radiographed is simultaneously obtained from different directions for tomographic imaging, and thus, by suitably summing the information, the desired layer can be sharpened to be imaged whereas the other superimposed layers remain blurred.

It should be noted that the concept "longitudinal axis of the object" in the claims and in the description refers in this connection to the longitudinal axis, or an axis parallel thereto, of that very part of the object which is to be radiographed. If, for instance, the object to be radiographed is the head of a patient or another part of the body itself, the longitudinal axis is that of the patient or an axis parallel thereto. If, however, the actual object to be radiographed is for instance a wrist or an ankle of a patient, the longitudinal axis is that of the particular limb itself. The dimensions of fan-shaped beam, on the other hand, are the width of the fan and the thickness thereof, whereby a narrow fan-shaped beam refers to narrowness in the thickness dimension of the fan.

Figure 2:
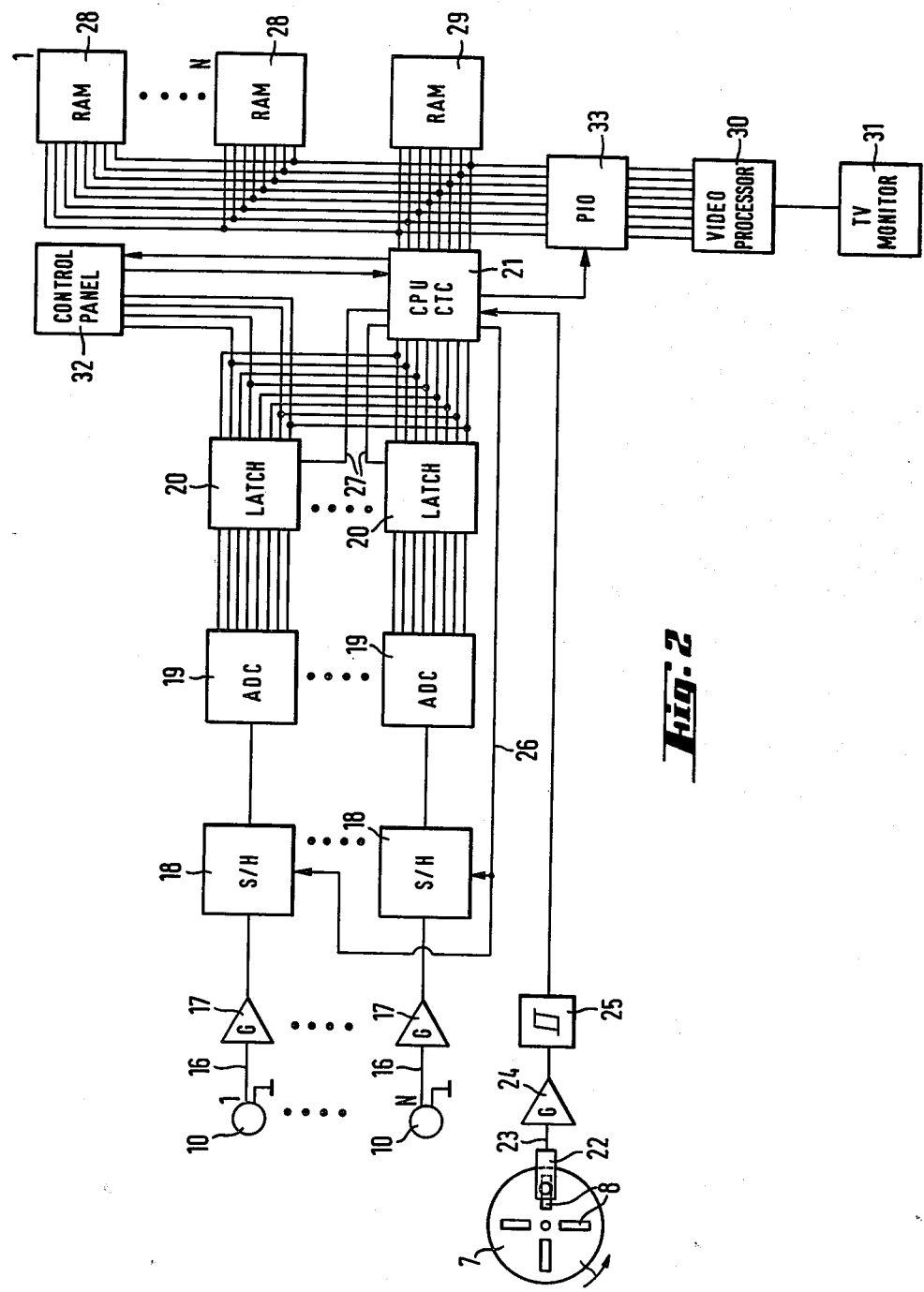

In the following the invention is described more in detail with reference to the attached drawing, in which FIG. 1 shows in principle an embodiment of the installation according to the invention and FIG. 2 shows the principles of processing the detected signals for the visualization of information.

The reference numeral 1 in the drawing indicates an X-ray tube or an analogous radiation generating means where a suitable radiation source, i.e. a focus 2 is bombed, for example, by an electron gun in a manner known as such for the purpose of generating X-rays or other penetrating radiation. The generated radiation is directed to the object to be radiographed by using a collimation unit 3 provided with collimating slots 5 for confining the beams to narrow, parallel X-ray fans. The shown embodiment includes also a disc-like element 7 driven by a motor 6 and provided with slots 8 for the purpose of confining the fanshaped X-ray beams in the longitudinal direction of the collimating slots 5 to narrow X-ray pencil beams 9 which, by the rotation of the element 7, are repeatedly displaced along the collimating slots 5. The installation also includes oblong detector units 10 corresponding to X-ray fans confined by collimating slots 5 for detecting and registering the X-rays passed through the object 4 to be radiographed. Thus, for each separate collimated pencil beam 9 there is an individual detector unit 10.

In the installation according to FIG. 1 the X-ray tube 1 and the detector units 10 are fixed to a frame unit 11 rotatably journalled to a body member 12 for rotation around the object 4 to be radiographed. The motor rotating the frame unit is not shown in the drawing. This installation is adapted for producing panoramic layer images, in other words the produced image defines a curved layer of the object. For producing images of ordinary planar layers in a simple way the X-ray generating means and the detector units can be attached, for example, to a cradle unit (not shown in Figures) moved laterally in relation to the object to be radiographed. In case it is desired to produce radiographs of panoramic image layers, the shape of which differs from cylindrical arc, so that the X-rays, nevertheless, are focused substantially perpendicularly on the layer to be visualized, the installation can be provided with means for independent movement of the frame unit 11 vertically. This movement can be accomplished by hydraulic or electric operation means 13 and the movement can be controlled by means of a rack 14. In practice this arrangement is also very advantageous for the reason that there is no need for special arrangements to support the patient during exposure, but almost any supporting means will do, for height adjustment is easy arranged with said vertical transfer movement of the frame unit 11. Patient positioning and focusing of the X-rays can be carried out by light-line means 15 or the like.

For better illustration of the collimating slots 5 and 8, their size is greatly exaggerated in FIG. 1. In practice the dimensions can be e.g. as follows: the length of the collimating slots 5 can be 50 mm and the width thereof 0.3 mm and the pitch between the slots 5 can be 1-10 mm, the distance of the slots from radiation generating means 2 can be appr. 300 mm and the distance of the detector units 10 from radiation generating means, i.e. from the focus 2, can be appr. 900 mm; in this case the pitch between the detector units 10 is 3-30 mm respectively. The slots 8 in the element 7 may be e.g. 0.3 mm in width. It is also possible to place the element 7 between the radiation generating means 2 and the collimating slots 5. The installation can be equipped, in addition to the collimation unit 3, with another collimator (not shown in Figures) to be placed between the detector units 10 and the object to be radiographed in order to eliminate possible diffuse scattered radiation. The detector unit 10 may be e.g. a sodiumiodide crystal (NaJ) provided with a photomultiplier tube either directly attached to the crystal or connected to it by a light cable for preamplifying the received information. Ionization chamber solutions are also well suited for the purpose allowing, if required, the chambers to be connectable to a united gas space. Another advantageous solution is to use some radiation responsive plate element (e.g. CsJ) and a photodiode in combination.

FIG. 2 gives as schematical representation an example of a system for processing and visualizing the information detected and registered by the detector units 10. In FIG. 2 the number of the detector units is generally N. Thus in the embodiment of FIG. 1, N=5.

For the preamplified signal 16 produced by detector units 10 respectively, the system includes amplifying circuit 17, means 18 for collecting and further transferring the information (sample/hold circuit), an analog-digital converter 19 and a latch unit 20 for feeding the information into a processor unit 21 provided with a counter/timer circuit.

For detecting the position of each narrow pencil beam 9 in the longitudinal direction of collimating slots 5 the installation includes sensor 22, e.g. of electro-optical or electromagnetic (inductive) construction, by means of which the position detection is arranged as a dependent variable of the transfer movement of slots 8 of the element 7. When the length of slots 8 of the element 7 are dimensioned so as to cover the united width of all the collimating slots 5, one signal 23 is sufficient for indicating the position of all the pencil beams 9 respectively at constant speed of the motor 6. To be exact the slots 8 are not displaced quite linearly along the length of the collimating slots 5. However, due to the small dimensions of the collimating slots the resulting errors in the position indication can be corrected, if required, by suitably timing the sampling from each detector unit so that mutually equally portioned signals are obtained. It should be noted that when such detector units 10 are used that include a plurality of separate detector elements arranged in the longitudinal direction of the collimating slots 5, a position detecting arrangement as described above is not necessarily needed. In this case, on the other hand, the resolution in the longitudinal direction of the collimating slots 5 is dependent on the dimensions of said detector elements. In both cases the rotation movement around the object to be radiographed in relation to the speed of sweeps of the pencil beams 9 and, consequently, the number of sweeps required should be small enough to enable scans in sufficiently quick succession for the required resolution. The frequency of sweeps can be increased by the number of slots 8 when bearing in mind, however, that the preceding slot 8 should reach the end of collimating slots 5 before the following slot 8 starts sweeping over said collimating slots 5.

The input of the position detecting signals 23 into the processor unit 21 is arranged through an amplifying circuit 24 and a trigger circuit 25. The trigger circuit 25 controls the processor unit 21 and its timer circuit (signal 26) to select the signals timed to be equally, portioned in respect to position to be transformed further from the sample/hold circuits. The processor unit 21 is also arranged to provide signals 27 for the latch circuits 20 so that correct signals are fed into the processor unit 21 respectively. The processor unit 21 includes means and programs known per se for processing and correcting the signals so that the values of the signals in respect to position can be normalized to correspond an even scale of gray in display when the absorption of radiation in the object is constant.

The information collected from each detector unit 10 is transferred by the processor unit 21 into separate memory units 28 respectively, in which the information is arranged according to the detected position information dependent on one hand on the sweeping movement of the pencil beams 9 along collimating slots 5 and on the other hand on the rotating movement of the pencil beams 9 around the object to be radiographed. In addition, the installation includes at least one memory unit 29 for the summation of the information produced by each detector unit 10 in accordance with the principles of tomosynthesis for visualization of the selected layer. Thus, by means of one single radiography any layer in the object to be radiographed can be visualized by manipulating the information collected in the memory units 28 with tomosynthesis technique. The principles of the summation are briefly outlined in the following.

Let us assume elements $a_{ij}$, $b_{ij}$, $c_{ij}$ . . . represent the basic information elements stored in the memory units 28 and collected from the detector units 10 respectively, whereby index i indicates position in the longitudinal direction of collimating slot 5 and index j indicates the number of the successive sweeps of pencil beam 9. Then elements $a_{1j}$ . . . $a_{nj}$, in which $j=1$ . . . m, represent vertical columns and elements $a_{i1}$ . . . $a_{im}$, in which $i=1$ . . . n, represent horizontal lines etc. The pencil beams 9 reach separate parts of the object at separate time and in somewhat different angle. The parameter due to this fact, the so called summing delay factor, which is dependent on the mutual distance of the collimating slots 5 and the speed of movement of the pencil beams 9 around the object to be radiographed, determines which vertical columns $a_{1j}$ . . . $a_{nj}$, $b_{1j}$ . . . $b_{nj}$, $c_{1j}$ . . . $c_{nj}$ etc., in which $j=1$ . . . m, are to be summed with one another respectively. At the same time the summing delay factor determines the layer selected to be visualized. Let a value d of summing delay factor represent the smallest difference between two separate layers, that is the difference between the sweeps of two successive pencil beams 9, summing and storing of elements $a_{ij}$, $b_{ij}$, $c_{ij}$ etc. into the memory unit 29 is arranged so that the general form of a summed element is $(a_{ij}+b_{i(j+1)}+c_{i(j+2)}+ \ldots )$. When using a summing delay factor $2d$ respectively the general form of an element summed and stored into the memory unit 29 is $(a_{ij}+b_{i(j+2)}+c_{i(j+4)}+ \ldots )$ etc.

The actual visualization of images can be accomplished with advantage by means of a videoprocessor 30 and a television monitor 31. The layer to be visualized can be selected with control panel 32. For speeding up the data transfer between the memory units 28, the memory unit 29 and the videoprocessor 30 the system can include a socalled input/output circuit 33, allowing simultaneous data transfer in both directions. When several memory units 29 and monitoring means are used it is possible to visualize simultaneously several separate layers.

The invention is not restricted to the embodiment disclosed but several modifications are feasible within the scope of the attached claims.

I claim:

1. Installation for producing radiographic layer images, said installation comprising: penetrating radiation generating means (1, 2), collimating means for collimating and for directing the radiation to an object to be radiographed, detecting means (10) for detecting penetrating radiation passed through the object, and information collecting, storing and processing means connectable to said detecting means (10) for storing and processing the detected information in a form for visualization thereof, said collimating means including a collimation unit (3) having at least two narrow, substantially parallel collimating slots (5) for collimating the radiation to fan-shaped beams, said slots being substantially in alignment with the longitudinal axis of the object so that one dimension of the images to be produced is determined by the length of said slots and, thus, by the width of the fan-shaped beams, said installation further including means (11, 13) for moving said radiation generating means (1, 2) and said collimating slots (5) together with said detecting means (10) around the object in mutual synchronization in a direction at least substantially orthogonal to the collimating slots, said direction defining the other dimension of the images to be produced, so that at least substantially all parts to be visualized in the object are radiated from a plurality of different directions by means of said narrow fan-shaped beams for obtaining information of a number of superimposed image layers, said information collecting, storing and processing means selecting the required layer or layers to be visualized on visualizing means.

2. An installation according to claim 1, the means for detecting and collecting the information contained in the radiation including an at least functionally separate detector unit (10) for each narrow fan-shaped beam, directed by the collimating slots respectively, said detector units (10) being opposite the radiation generating means in relation to the object (4) to be radiographed and moved dependent on the movements of said collimating slots (5), the fan-shaped beams defined by the collimating slots being focused on the axis of the detector units respectively.

3. An installation according to claim 2, wherein said detector units (10) are successively aligned in the width direction of the narrow fan-shaped beams.

4. An installation according to claim 2, wherein said detector unit (10) includes an oblong conversion element focused on the fan-shaped beam and responsive to radiation passed through the object to be radiographed, said conversion element being a NaJ scintillation crystal optically connected to a photomultiplier tube.

5. An installation according to claim 3, wherein the fan-shaped beam defined by a collimating slot (5) is so dimensioned that the thickness of the fan-shaped beam corresponds to the width of the smallest detector unit.

6. An installation according to claim 2, the installation including, for processing the information detected by a detector unit, an amplifier circuit (17), means for collecting the amplified information and for feeding it into an analog-digital converter (19), a latch unit (20) for feeding the information into a processor unit (21) arranged to control the transfer and processing of the information, the installation further including means (28) for separate storage of information derived from each detector unit.

7. An installation according to claim 1, the installation including, for producing tomographic images, a memory unit (29) for summing the stored information derived from the object to be radiographed in accordance with a summing delay factor, determined by the selected image layer to be visualized and representative of the mutual projection differences between the fan-shaped beams and, thus, the differences between the detector units as well, and means for the visualization of the respective layer images stored in said memory unit (29).

8. An installation according to claim 2, said collimation unit (3) being arranged in fixed relationship with the radiation generating means (2) and being provided with means for confining the collimated fan-shaped beams to narrow pencil beams (9) in the longitudinal direction of the collimating slots, said means confining the narrow pencil beams being arranged to move the narrow pencil beams, directed to an object to be radiographed, repeatedly along said collimating slots.

9. An installation according to claim 8, said means defining the narrow pencil beams (9) comprising a movable element (7) of radiation opaque material, placed between the radiation generating means (2) and the object to be radiographed, preferably perpendicularly to the collimating slots (5), and provided with one or several radiation penetrable slots (8), the width of which defines the second dimension of the pencil beam (9) and the length of which is chosen to cover the united width of all the collimating slots in all positions of sweeps over the collimating slots.

10. An installation according to claim 8, said installation including means for detecting the location of the pencil beams (9) in relation to the collimating slots (5) and the detector units (10), said means being arranged to detect the location of the means defining the pencil beams (9) as a dependent variable of the transfer movement thereof and to generate a signal (23) for controlling transfer of the information derived from the detector units (10).

11. An installation according to claim 1, the width of a collimating slot (5) in relation to its length being 0.001 ... 0.01.

12. An installation according to claim 1, the dimensions of the field defined by the collimating slots (5) of the collimation unit (3) being in the longitudinal direction of the slots 20 ... 200 mm and the distance between the outermost slots in the transversal direction thereof being 5 ... 50 mm.

13. An installation according to claim 1, the pitch between the collimating slots (5) being 1 ... 10 mm and the distance of the collimating slots (5) from the radiation source being 200 ... 500 mm.

14. An installation according to claim 1, said installation including means (13) for transferring the radiation generating means (2) and the detector units (10) in transverse direction in relation to the object (4) to be radiographed.

15. The invention according to claim 2 wherein said detector units are mechanically connected to said collimating slots.

16. The invention according to claim 15 wherein said detector units and said collimating slots are mechanically fixed to a common frame unit.

17. The invention according to claim 11 wherein the width of a collimating slot in relation to its length is 0.003 ... 0.006.

18. The invention according to claim 12 wherein the distance between the outer most slots in the transversal direction thereof is 10 ... 20 mm.

* * * * *

UNITED STATES PATENT AND TRADEMARK OFFICE
CERTIFICATE OF CORRECTION

PATENT NO. : 4,481,650
DATED : November 6, 1984
INVENTOR(S) : ILMARI KINNANEN

It is certified that error appears in the above-identified patent and that said Letters Patent are hereby corrected as shown below:

Cover Page at [73] "Assignee: INSTRUMENTARLUM OY, Finland" should read ---"Assignee: INSTRUMENTARIUM OY, Finland---

Col. 1, Line 62 Delete"The" and substitute therefor ---In---

Col. 7, Line 8 CLAIM 4, Delete "said" and substitute therefor ---each---

Signed and Sealed this

Seventh Day of May 1985

[SEAL]

Attest:

DONALD J. QUIGG

*Attesting Officer*     *Acting Commissioner of Patents and Trademarks*